(12) United States Patent
Kim et al.

(10) Patent No.: US 11,655,430 B2
(45) Date of Patent: *May 23, 2023

(54) COATING COMPOSITION FOR PRODUCING ARTICLE

(71) Applicant: Industry-University Cooperation Foundation Hanyang University, Seoul (KR)

(72) Inventors: Dong Rip Kim, Seoul (KR); Kang Won Lee, Seoul (KR); Ji Hoon Ahn, Jeju-si (KR); Yale Jeon, Incheon (KR)

(73) Assignee: Industry-University Cooperation Foundation Hanyang University, Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 17/543,219

(22) Filed: Dec. 6, 2021

(65) Prior Publication Data

US 2022/0154095 A1    May 19, 2022

Related U.S. Application Data

(63) Continuation of application No. 16/756,574, filed as application No. PCT/KR2018/012278 on Oct. 17, 2018, now Pat. No. 11,225,628.

(30) Foreign Application Priority Data

Oct. 17, 2017   (KR) .................. 10-2017-0134378
Oct. 15, 2018   (KR) .................. 10-2018-0122484

(51) Int. Cl.
  *C10M 169/02*   (2006.01)
  *A61M 25/00*   (2006.01)
  (Continued)

(52) U.S. Cl.
  CPC ...... *C10M 169/02* (2013.01); *A61M 25/0045* (2013.01); *C10M 107/32* (2013.01);
  (Continued)

(58) Field of Classification Search
  CPC combination set(s) only.
  See application file for complete search history.

(56) References Cited

U.S. PATENT DOCUMENTS 6,458,867 B1 * 10/2002 Wang ............... A61F 2/966
                                                523/105
11,225,628 B2 * 1/2022 Kim ................. C10M 107/32
(Continued)

FOREIGN PATENT DOCUMENTS

JP       2002-98189 A      4/2002
KR   10-2011-0048545 A      5/2011
(Continued)

OTHER PUBLICATIONS

International Search Report for PCT/KR2018/012278 dated May 20, 2019 (PCT/ISA/210).

*Primary Examiner* — Ellen M McAvoy
(74) *Attorney, Agent, or Firm* — Sughrue Mion, PLLC

(57) ABSTRACT

A coating composition for producing an article is disclosed. The coating composition includes a blend of a polymer resin and a lubricating oil, wherein the coating composition is in a liquid-phase By using the coating composition, it is possible to produce the article which can be used in various industries, only with a simple process of molding and curing a polymer resin by the technique of the prior art.

10 Claims, 13 Drawing Sheets

(51) Int. Cl.
  *C10M 107/32* (2006.01)
  *C10M 107/38* (2006.01)
  *C10M 107/50* (2006.01)
  *C10M 113/12* (2006.01)
  *C10N 40/00* (2006.01)
  *C10N 50/08* (2006.01)

(52) U.S. Cl.
  CPC ........ *C10M 107/38* (2013.01); *C10M 107/50* (2013.01); *C10M 113/12* (2013.01); *A61M 2025/0046* (2013.01); *C10M 2201/1056* (2013.01); *C10M 2209/1023* (2013.01); *C10M 2213/0623* (2013.01); *C10M 2229/0415* (2013.01); *C10N 2040/50* (2020.05); *C10N 2050/08* (2013.01)

(56) References Cited

U.S. PATENT DOCUMENTS

| | | | |
|---|---|---|---|
| 2006/0240060 A1* | 10/2006 | Bavaro | A61L 29/14 424/422 |
| 2009/0171302 A1* | 7/2009 | Eramo, Jr. | C09D 4/00 606/1 |
| 2009/0295032 A1 | 12/2009 | Hopkins | |
| 2014/0187666 A1 | 7/2014 | Aizenberg et al. | |
| 2014/0342954 A1 | 11/2014 | Ingber et al. | |
| 2015/0152270 A1 | 6/2015 | Aizenberg et al. | |
| 2015/0232782 A1* | 8/2015 | Fisher | C10M 169/042 508/208 |
| 2016/0144079 A1 | 5/2016 | Ingber et al. | |
| 2016/0201005 A1 | 7/2016 | Nowak et al. | |
| 2016/0263285 A1* | 9/2016 | Rostami | A61L 29/049 |
| 2017/0037257 A1 | 2/2017 | Yang et al. | |
| 2017/0081534 A1 | 3/2017 | Shah et al. | |
| 2017/0298586 A1 | 10/2017 | Villar et al. | |
| 2018/0094204 A1 | 4/2018 | Larimer et al. | |
| 2018/0163152 A1* | 6/2018 | Luo | C09D 129/14 |
| 2018/0230318 A1 | 8/2018 | Lynn et al. | |
| 2018/0237659 A1 | 8/2018 | Kim et al. | |
| 2019/0168258 A1 | 6/2019 | Kim et al. | |
| 2019/0211154 A1* | 7/2019 | Lawton | C09D 5/08 |

FOREIGN PATENT DOCUMENTS

| | | |
|---|---|---|
| KR | 10-1272029 B1 | 6/2013 |
| KR | 10-2014-0004723 A | 1/2014 |
| KR | 10-1350993 B1 | 1/2014 |
| KR | 10-2015-0033725 A | 4/2015 |
| KR | 10-2015-0098142 A | 8/2015 |
| KR | 10-2016-0029494 A | 3/2016 |

\* cited by examiner

COATING COMPOSITION FOR PRODUCING ARTICLE

CROSS REFERENCE TO RELATED APPLICATIONS

This application is a Continuation of U.S. application Ser. No. 16/756,574 filed Apr. 16, 2020 (allowed), which is a National Stage of International Application No. PCT/PCT/KR2018/012278 filed Oct. 17, 2018, claiming priority based on Korean Patent Application No. 10-2017-0134378, filed Oct. 17, 2017 and Korean Patent Application No. 10-2018-0122484 filed Oct. 15, 2018.

TECHNICAL FIELD

The present invention relates to a coating composition for producing an article having a slippery surface, and more particularly, to a coating composition that can produce an article having an inner surface and an outer surface, both of which are slippery, in a simple process.

Further, the present invention is directed to a 3D printing composition for producing a 3D article having a slippery surface and a method for preparing the same, and more specifically, to a 3D printing composition that can produce an article of a 3D shape having an inner surface and an outer surface, both of which are slippery, and a method for preparing the same.

BACKGROUND ART

A development of a liquid-repellent surface has been promoted by a self-clean ability to the surface of an animal, an insect and a plant. The liquid-repellent surface includes a water-repellent surface first inspired by a lotus effect. The water-repellent surface has a structure in which a water droplet can easily roll down due to a microstructure of the surface and a low surface energy. The water-repellent surface has been continuously studied to improve its performance in various fields that require self-cleaning, but has problems such as a durability required to implement a super water repellence and a fluorinated compound harmful to the human body.

A research on the slippery surface has been actively conducted since the concept of SLIPS at Harvard University in 2011 was introduced. Such a concept naturally imitates the surface of a bug's dung grass, which exerts the self-cleaning ability that easily rolls down even at a small sliding angle of droplets due to the presence of a lubricating layer on the surface.

The slippery surface has many advantages such as an anti-biofouling and a low ice adhesion, but most researches are mainly focused on a coating technique of a two-dimensional surface, and as a result, an application to a three-dimensional shape has been limited. Therefore, the realization of the slippery surface in various three-dimensional shapes is necessary in an industry requiring the self-cleaning.

Korean Patent Laid-open Publication No. 10-2014-0004723 discloses a technology that a self-recovering and scratch-resistant slippery surface is formed by working a chemically inert high-density coating liquid on a roughened solid surface, characterized by a micro and nanoscale photography. However, since the technology is implemented in a two-dimensional surface, it is difficult to implement various complex three-dimensional shapes, and since the technology forms a slippery surface by carrying out a coating through an immersion, in case of a shape such as a circular pipe with a small inner diameter, there is a disadvantage that it is difficult to form the slippery surface inside the circular pipe uniformly.

Further, Korean Patent Laid-open Publication No. 10-2011-0048545 relates to a use of a slippery thin film or a coating for improving lubricity in an area where friction and abrasion occur, wherein the film is made by coating of nanoparticles and coating of a lipophilic layer. However, the technology is to implement a lubricating layer of the two-dimensional surface, not the three-dimensional shape, and has a disadvantage that it is limited to a vaper deposition technique and a coating technique.

Meanwhile, a 3D printer is the equipment that produces an actual three-dimensional shape as it is, based on an input three-dimensional drawing like printing a letter or picture. Recently, the 3D printing technology has become a central issue that leads the 4th industrial revolution, and has been widely used to make various models in an automobile field, a medical field, an art field, and an education field.

A principle of the 3D printer can be comprehensively classified into a cutting type and a laminated type, and most of the 3D printers that are actually applied correspond to the laminated type without loss of a material.

There are about 20 modes that use the principle of the laminated type, but among them, the most used modes are a SLA (Stereolithography Apparatus), a FDM (Fused Deposition Modeling) or a FFF (Fused Filament Fabrication) and a SLS (Selective Laser Sintering).

The SLA is a mode that projects and mold a laser beam in a water tank containing a liquid photocurable resin, wherein an epoxy-typed photopolymer is mainly used as the photocurable resin. Meanwhile, the FDM (or FFF) is a mode that is molded in a three-dimension by injecting a material of a filament and discharging the injected material in a molten state from a nozzle of a printer which moves in the Z, Y and Z axes, and uses a thermoplastic plastic as a main material. Further, the SLS implements the 3D printing with a mode that selectively sinters a powdery material such as a metal, a plastic, and a ceramic by projecting the laser beam in the water tank containing the powdery material.

Among the above three modes, the FDM mode which uses by producing the thermoplastic plastic in the form of the filament is the most widely popular, because a price of the 3D printer is relatively cheap and the FDM mode has a faster printing speed than other modes. The FDM mode has usefully employed materials such as a polylactic acid (PLA), an acrylonitrile butadiene styrene (ABS), a high density polyethylene (HDPE), and a polycarbonate (PC), for the reasons that the above materials generally provide an excellent bed adhesion and an excellent interlayer adhesion as well as a good shape stability when they are formed into a 3D structure.

Patent documents related to a 3D printing material used in the FDM mode may include Korean Patent Laid-open Publication No. 10-2015-0098142 (FDM-typed composite filament composition for 3D printer containing metal powder), Korean Patent Registration Publication No. 10-1350993 (Method of producing PLA filament for 3D printer having flame retardant and heat-resistant properties using microcapsules and PLA filament produced by same method), U.S. Patent Application Publication No. 2009/0295032 (Method for producing 3D object using modified ABS material), and the like.

The inventors of the present invention have researched to realize an article having a slippery surface even to the inside thereof, and, as a result, found that an article having an inner surface and an outer surface, both of which are slippery, can be produced in a simple technique by using a coating composition comprising a blend of a polymer resin and a lubricating oil, to complete the present invention.

DETAILED DESCRIPTION OF THE INVENTION

Technical Problem

An object of the present invention for solving the above challenges is to provide a coating composition that can produce an article having a slippery surface even to the inside thereof in a simple process.

Other object of the present invention is to provide an article having a slippery surface.

Further, an object of the present invention is to provide a composition for 3D printing that can produce an article of a three-dimensional shape having a slippery surface even to the inside thereof in a simple process.

Another object of the present invention is to provide a method for producing a composition for 3D printing having a slippery surface.

Technical Solution

In order to attain the above objects, the present invention provides a coating composition for producing an article having a slippery surface, which comprises a blend of a polymer resin and a lubricating oil as a composition In the present invention, the coating composition may further comprise an aerogel.

In the present invention, the polymer resin may comprise one or more selected from the group consisting of polydimethylsiloxane (PDMS), silicone, perfluoropolyether (PFPE), polyurethane (PU), polylactic acid (PLA), acrylonitrile butadiene styrene (ABS), high density polyethylene (HDPE), polycarbonate (PC), polystyrene (PS), polyester, polyolefin, polyamide, polyvinyl alcohol, N-vinyl pyrrolidone, N-vinyl caprolactam, dimethylacrylamide, hydroxyethylacrylamide, 2-acryloyloxyethyl isocyanate, isobornyl acrylate, tetrahydrofurfuryl acrylate, phenoxypolyethylene glycol acrylate, lauryl acrylate, benzyl acrylate, ethoxyethyl acrylate, phenoxyethyl acrylate, cyclic trimethylolformal acrylate, 6-hexanediol diacrylate, trimethylolpropane triacrylate, pentaerythritol tetraacrylate, tripropylene glycol diacrylate, tetraethylene glycol diacrylate, 1,1-(bisacryloyloxymethyl)ethyl isocyanate, polyester acrylate, and urethane acrylate.

In the present invention, the lubricating oil may comprise one or more selected from the group consisting of an olive oil, a fluorinated oil, a silicone oil, an essential oil, a paraffin oil, and a mineral oil.

In the present invention, the aerogel may comprise one or more selected from a silica gel, a carbon aerogel and a graphene aerogel.

The coating composition of the present invention may comprise 30 to 100 parts by weight of the lubricating oil based on 100 parts by weight of the polymer resin.

The coating composition of the present invention may further comprise 1 to 200 parts by weight of the aerogel based on 100 parts by weight of the lubricating oil.

The coating composition of the present invention may comprise the essential oil of 10 to 100% by weight based on the total weight of the lubricating oil.

The coating composition of the present invention may further comprise one or more solvents selected from the group consisting of dichloromethane (DCM), tetrahydrofuran, dioxane, methylethylketone (MEK), and dimethylformamide (DMF).

In the present invention, the solvent may be contained such that a concentration of the total composition is 0.05 to 0.30 g/mL.

The present invention also provides an article having a slippery surface, which is formed by curing a coating composition comprising a blend of a polymer resin and a lubricating oil.

In the present invention, the coating composition may further comprise an aerogel.

The article having the slippery surface according to the present invention may have a light transmission of 80% or more.

The article having the slippery surface according to the present invention may comprise 10 to 100% by weight of the essential oil based on the total weight of the lubricating Oil.

The article having the slippery surface according to the present invention may further comprise a material through which the lubricating oil is impermeable.

The present invention also provides a medical catheter having a slippery surface, which is formed by curing a coating composition comprising a blend of a polymer resin and a lubricating oil, the medical catheter comprising 10 to 30% by weight of an essential oil based on the total weight of the lubricating oil.

The present invention provides a 3D printing composition for producing a three-dimensional article having a slippery surface, the 3D printing composition comprising a polymer resin and an oil.

In the present invention, the 3D printing composition may comprise 30 to 100 parts by weight of the oil based on 100 parts by weight of the polymer resin.

In the present invention, the polymer resin may be selected from polylactic acid (PLA), acrylonitrile butadiene styrene (ABS), high density polyethylene (HDPE), polycarbonate (PC), polyurethane (PU), polystyrene (PS), polyester, polyolefin, polyamide, polyvinyl alcohol, and a combination thereof.

Alternatively, in the present invention, the polymer resin may be a photocurable polymer selected from the group consisting of N-vinyl pyrrolidone, N-vinyl caprolactam, dimethylacrylamide, hydroxyethylacrylamide, 2-acryloyloxyethyl isocyanate, isobornyl acrylate, tetrahydrofurfuryl acrylate, phenoxypolyethylene glycol acrylate, lauryl acrylate, benzyl acrylate, ethoxyethyl acrylate, phenoxyethyl acrylate, cyclic trimethylolformal acrylate, 6-hexanediol diacrylate, trimethylolpropane triacrylate, pentaerythritol tetraacrylate, tripropylene glycol diacrylate, tetraethylene glycol diacrylate, 1,1-(bisacryloyloxymethyl)ethyl isocyanate, polyester acrylate, and urethane acrylate.

In the present invention, the oil may be one or more selected from an olive oil, a silicone oil, a paraffin oil and a mineral oil.

In the present invention, the 3D printing composition may further comprise 1 to 20 parts by weight of an aerogel based on 100 parts by weight of the oil.

In the present invention, the aerogel may be one or more selected from a silica gel, a carbon aerogel and a graphene aerogel.

In the present invention, the 3D printing composition may further comprise one or more solvents selected from the group consisting of dichloromethane (DCM), tetrahydrofuran, dioxane, methylethylketone (MEK) and dimethylformamide (DMF).

In the present invention, the solvent may be contained such that a concentration of the total composition is 0.05 to 0.30 g/mL.

The present invention also provides a method of preparing a 3D printing composition for producing a three-dimensional article having a slippery surface, the method comprising the steps of: preparing a polymer solution by dissolving a polymer resin in a first solvent; preparing an oil solution by dissolving an oil in a second solvent; and blending the polymer solution and the oil solution.

In the present invention, the step of preparing the oil solution may comprise adding an aerogel to the second solvent.

In the present invention, the first solvent and the second solvent may each independently be one or more selected from dichloromethane (DCM), tetrahydrofuran, dioxane, methylethylketone (MEK), and dimethylformamide (DMF).

In the present invention, the first solvent and the second solvent may be the same solvent.

In the present invention, a concentration of the polymer solution may be 0.03 to 0.30 g/mL.

In the present invention, a concentration of the oil solution may be 10 to 50% (v/v).

The present invention also provides a filament for a 3D printer comprising a 3D printing composition for producing a three-dimensional article having a slippery surface.

In the present invention, a diameter of the filament may be 0.8 to 4.0 mm.

Effects of the Invention

By using a coating composition according to the present invention, it is possible to produce an article having an inner surface and an outer surface, both of which are slippery, only with a simple process of molding and curing a polymer resin by the technique of the prior art. The article produced using the coating composition of the present invention can solve an ice removal on a surface of the machinery such as an aircraft and an automobile, a biofouling problem in a blood vessel, a problem requiring self-cleaning, and the like, and thus can be used in various industries.

DETAILED DESCRIPTION

Hereinafter, a concrete aspect of the present invention will be described in more detail. Unless defined otherwise, all technical and scientific terms used in the present specification have the same meanings as those commonly understood by a person who is skilled in the technical field to which the present invention pertains. In general, the nomenclature used in the specification is well known and commonly used in the present technology field.

The present invention relates to a composition for producing an article having a slippery surface.

The composition of the present invention comprises a blend of a polymer resin and a lubricating oil.

In the present invention, the slippery surface means a surface having a self-cleaning ability that droplets easily roll down even at a small sliding angle without adherence of a water or an ice because the surface of the article contains a lubricating oil.

In the present invention, the term "blend" refers to a state in which two or more materials that do not dissolve with each other are uniformly dispersed.

According to the present invention, a blend of a polymer resin and a lubricating oil uniformly blended with each other is provided as a coating composition and the coating composition is coated to form a desired article, whereby the article can have a slippery surface.

In general, a miscibility of the above two materials can be calculated as a free energy for blending as follows.

$$\Delta G_{mix} = \Delta H - T\Delta S$$

If the free energy for blending is greater than zero, it is difficult for the two materials to blend with each other. This means that a large interfacial tension acts between the two materials so that they are preferably separated rather than uniformly blended.

It has been found by the present invention that the interfacial tension of the two materials with a free energy for blending greater than zero can be offset by using a porous aerogel as a compatibilizer. The porous aerogel has nano-sized pores that provide an extremely large surface area (about 310 m$^2$/g), and also has an excellent oil adsorption property due to its chemical affinity.

In case the aerogel is added to the blend, the free energy for blending can be determined as follows.

$$\Delta G_{mix} = \Delta G_{PS} + \Delta G_{LS} + \Delta G_{PL}$$

(P: polymer, L: lubricating oil, S: solid particles)

Therefore, the Gibbs energy is changed to less than 0, and the lubricating oil and the polymer resin can be stably blended.

Figure 1:
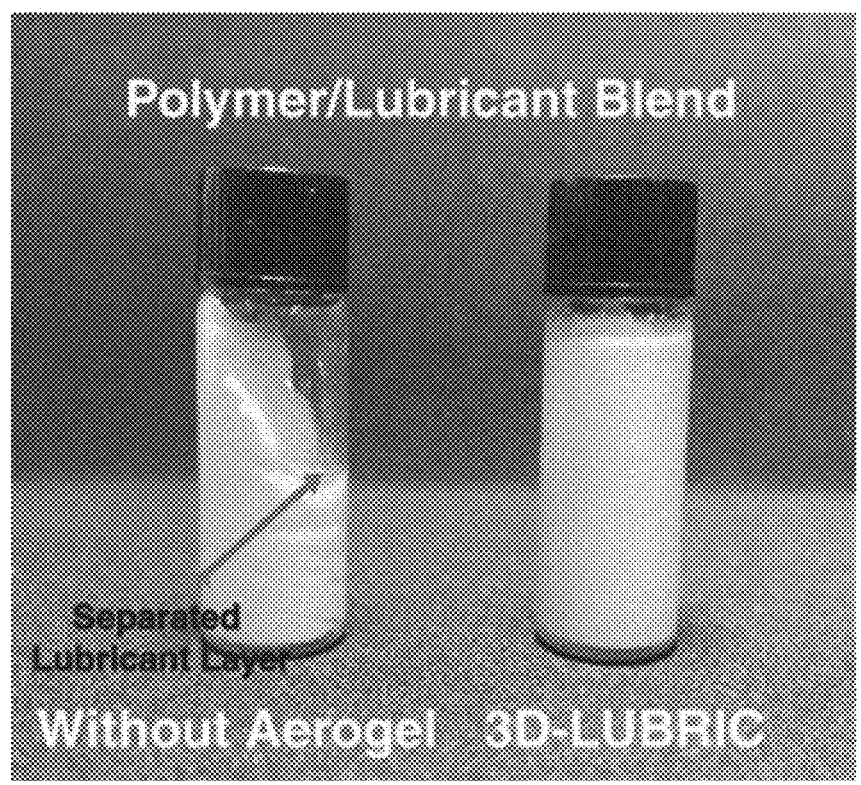
FIG. 1 shows a state of a blend of a polymer resin and a lubricating oil with or without addition of an aerogel.

The left glass bottle in FIG. 1 shows a blend of a polymer resin (PDMS) and a lubricating oil (olive oil) without addition of an aerogel. It can be confirmed that the two materials indicate phase separation without being uniformly blended. On the other hand, the right glass bottle to which the aerogel (silica gel) is added can be visually confirmed that the three materials maintain a uniform blend.

It is preferred that the lubricating oil uses an olive oil, a fluorinated oil, a silicone oil, an essential oil, a paraffin oil, a mineral oil, and the like.

In the present invention, the "lubricating oil" may be used in the same meaning as an "oil" in some cases.

The essential oil may include a clove oil, and the paraffin oil may be selected from n-octane, n-decane, n-dodecane, hexadecane, octadecane, and the like, and the mineral oil may be selected from a diesel, a gasoline, a crude oil, and the like.

If the essential oil, in particular, the clove oil, is used as the lubricating oil, an antibacterial effect can be exerted to the produced article.

In the present invention, the lubricating oil is preferably used by adjusting a desired content according to a degree of slipperiness of the article to be produced, and may be contained in 10 to 200 parts by weight based on 100 parts by weight of the polymer resin. Preferably, the lubricating oil may be contained in 30 to 100 parts by weight based on 100 parts by weight of the polymer resin.

The aerogel may include a silica gel, a carbon aerogel, a graphene aerogel, or the like. The aerogel absorbs the lubricating oil and helps the lubricating oil to stably blend with the polymer resin and prevents the lubricating oil from evaporating easily even after being commercialized.

Further, the aerogel can improve a mechanical property of the produced article. In an embodiment of the present invention, it was confirmed that the mechanical properties such as a storage elastic force, a tensile strength, and a hardness of the article comprising the aerogel can be greatly improved. Therefore, when producing a three-dimensional article using the coating composition of the present invention, the aerogel allows the polymer to maintain the desired shape until it is crosslinked/cured.

The aerogel is preferably added in an appropriate amount in consideration of a miscibility of the polymer resin and the lubricating oil and the mechanical property of the article to be produced, and may be added in an amount of 1 to 200 parts by weight based on 100 parts by weight of the oil.

In the present invention, the polymer resin may include a liquid polymer such as polydimethylsiloxane (PDMS), silicone, perfluoropolyether (PFPE), polyurethane (PU), polyimide (PI), and the like. The liquid polymer may be blended with the lubricating oil without a separate solvent, and may be blended with the lubricating oil by the aerogel, if necessary.

For example, a silicone elastomer and a silicone oil are excellent in the miscibility even without addition of the aerogel and can be used in the coating composition of the present invention, but the silicone elastomer and the olive oil are not blended without addition of the aerogel.

The polymer resin of the present invention may also use a thermoplastic polymer resin selected from polylactic acid (PLA), acrylonitrile butadiene styrene (ABS), high density polyethylene (HDPE), polycarbonate (PC), thermoplastic polyurethane (TPU), polystyrene (PS), polyester, polyolefin, polyamide, polyvinyl alcohol, and a combination thereof.

In case the thermoplastic polymer resin is used as the polymer resin, it is preferable to dissolve a solid polymer in a solvent to liquefy it and blend the liquified polymer with the lubricating oil. The solvent which can be used in the present invention may include dichloromethane (DCM), tetrahydrofuran (THF), dioxane, methyl ethyl ketone (MEK), dimethylformamide (DMF), or the like.

In order to select a suitable solvent that can be blended with the lubricating oil simultaneously with liquefying the solid polymer, a Flory-Huggins solution may be applied. The Flory-Huggins constant ($\chi$) is defined as follows:

$$\chi = \frac{(\delta_1 - \delta_2)^2 V_1}{RT}$$

In the above formula, $\delta_1$ and $\delta_2$ represent solubility constants of a solvent and a solute, $V_1$ represents a molar volume of the solvent, R represents a gas constant, and T represents an absolute temperature.

The smaller the $\chi$ value, the better the solvent and the solute can be dissolved.

For example, the $\chi$ of polylactic acid (PLA) and dichloromethane (DCM) is 0.03, which is much less than 0.42 that is the $\chi$ of PLA and toluene. Therefore, it can be seen that DCM is more suitable than an acetone so as to dissolve the PLA.

Further, the constant $\chi$ between the DCM and the lubricating oil is also important for blending. It can be seen that the olive oil ($\chi=0.47$) and the mineral oil ($\chi=0.91$) are easier to blend with the DCM than a water ($\chi=21.43$) or ethylene glycol ($\chi=6.08$).

The solvent is preferably added in such an amount that a concentration of the total composition becomes 0.05 to 0.30 g/mL, more preferably, 0.05 to 0.15 g/mL.

Table 1 below shows a type of the solvent suitable for the solid polymer resin.

TABLE 1

| Polymer | Solvent |
|---|---|
| polylactic acid (PLA) | dichloromethane (DCM), tetrahydrofurandioxane |
| acrylonitrile butadiene styrene (ABS) | DCM, methyl ethyl ketone (MEK) |
| polyurethane (PU) | dimethylformamide (DMF) |
| polystyrene (PS) | DCM |
| Acrylic | MEK |
| Polycarbonate (PC) | DCM, MEK |

A method for preparing a coating composition of the present invention using a solid polymer resin comprises the steps of dissolving the polymer resin in a first solvent to prepare a polymer solution; and blending the polymer solution and a lubricating oil.

In the above method, the step of blending the lubricating oil may include blending a lubricating oil solution formed by dissolving the lubricating oil in a second solvent.

In a preferred embodiment of the present invention, the step of blending the lubricating oil is preferably further blended with an aerogel, and it is most preferred to blend the polymer resin solution and the lubricating oil solution after adding the aerogel to the lubricating oil solution.

According to the present invention, the polymer resin is dissolved in the solvent to form a liquid phase at a room temperature and the lubricating oil is dissolved in a separate solvent to form a liquid phase, and then the polymer resin and the lubricating oil in the liquid phase are blended such that the polymer resin is well blended with the lubricating oil, whereby it is possible to prevent the polymer resin from curing easily or the lubricating oil from evaporating easily at a high temperature.

The first solvent and the second solvent are preferably the same solvent.

The lubricating oil solution preferably has a concentration of 10 to 50% (v/v), more preferably 15 to 30% (v/v).

In the present invention, the blending of the above two solutions is preferably continuously stirred while adding the polymer solution to the lubricating oil solution little by little.

The polymer resin may also use a photocurable polymer resin depending on the application. Examples of the photocurable polymer may include a nitrogen-containing vinyl compound such as N-vinyl pyrrolidone and N-vinyl caprolactam, dimethylacrylamide, hydroxyethylacrylamide, 2-acryloyloxyethyl isocyanate, isobornyl acrylate, tetrahydrofurfuryl acrylate, phenoxypolyethylene glycol acrylate, lauryl acrylate, benzyl acrylate, ethoxyethyl acrylate, phenoxyethyl acrylate, cyclic trimethylolformal acrylate, 6-hexanediol diacrylate, trimethylolpropane triacrylate, pentaerythritol tetraacrylate, tripropylene glycol diacrylate, tetraethylene glycol diacrylate, 1,1-(bisacryloyloxymethyl) ethyl isocyanate, polyester acrylate, urethane acrylate, and the like.

The coating composition of the present invention may also, if necessary, further include one or more additives selected from the group consisting of a thermal stabilizer, an antioxidant, a light stabilizer, a mold releasing agent, a compatibilizer, a dye, a pigment, a colorant, a plasticizer, an impact modifier, a stabilizer and a lubricant.

Moreover, in case the photocurable polymer resin is used, it is preferable to further contain a photo initiator.

The coating composition of the present invention may be commercialized by a known method. For example, in case a film having a slippery surface is to be produced, the coating composition may be molded using a known molding technique, and then the polymer resin used may be cured to produce an article.

The molding may use various known molding techniques such as a coating, a molding, and a 3D printing.

The coating composition comprising a thermosetting polymer resin may be molded into a shape of the article using the molding, and then crosslinked by a heat to produce an article having a slippery surface. Similarly, in case the coating composition comprises a photocurable polymer resin, the article having the slippery surface may be produced by a photocuring.

Depending on a kind of the polymer resin and the lubricating oil, the coating composition of the present invention can produce an article having a characteristic such as an optical transparency, a stretchability, a flexibility, an ice non-adhesiveness, and an antibacterial/sterile property. In particular, in an embodiment of the present invention, it was confirmed that a PDMS-based article having a lubricant property exhibits a light transmittance of 88% or more at a wavelength of 300 to 800 nm.

In a preferred embodiment of the present invention, the coating composition may be a 3D printing composition for producing an article of a three-dimensional shape having a slippery surface.

In the present invention, the article of the three-dimensional shape having the slippery surface means the three-dimensional article having not only an outer surface but also an inner surface, both of which are slippery.

The aerogel available for the 3D printing composition of the present invention preferably has a particle size of 20 to 200 μm. If the particle size of the aerogel is less than 20 μm, it is difficult to sufficiently absorb the oil, and if it is 200 μm or more, there is a problem in that a nozzle of the 3D printer is clogged by the particle size so that a smooth spraying cannot be achieved.

The 3D printing composition of the present invention may also, if necessary, further include one or more additives selected from the group consisting of a thermal stabilizer, an antioxidant, a light stabilizer, a mold releasing agent, a compatibilizer, a dye, a pigment, a colorant, a plasticizer, an impact modifier, a stabilizer and a lubricant.

Moreover, in case the photocurable polymer resin is used, it is preferable to further contain a photo initiator.

The polymer resin is not particularly limited as long as it is the polymer resin that can be used in the 3D printing composition, and in case the polymer resin is applied to a 3D printer of a FDM mode, it is preferable to use a thermoplastic polymer resin selected from polylactic acid (PLA), acrylonitrile butadiene styrene (ABS), high density polyethylene (HDPE), polycarbonate (PC), polyurethane (PU), polystyrene (PS), polyester, polyolefin, polyamide, polyvinyl alcohol and a combination thereof. Among them, the polylactic acid (PLA) is most preferred in terms of stability.

Further, in case the polymer resin is applied to a photocuring-typed 3D printer, it is also possible to use a photocurable polymer resin. Examples of the photocurable polymer resin may include a nitrogen-containing vinyl compound such as N-vinyl pyrrolidone and N-vinyl caprolactam, dimethylacrylamide, hydroxyethylacrylamide, 2-acryloyloxyethyl isocyanate, isobornyl acrylate, tetrahydrofurfuryl acrylate, phenoxypolyethylene glycol acrylate, lauryl acrylate, benzyl acrylate, ethoxyethyl acrylate, phenoxyethyl acrylate, cyclic trimethylolformal acrylate, 6-hexanediol diacrylate, trimethylolpropane triacrylate, pentaerythritol tetraacrylate, tripropylene glycol diacrylate, tetraethylene glycol diacrylate, 1,1-(bisacryloyloxymethyl) ethyl isocyanate, polyester acrylate, and urethane acrylate.

The oil may be contained in an amount of 30 to 100 parts by weight, preferably 50 to 80 parts by weight, based on the weight of the polymer resin. If the oil is too small amount, a slipperiness of the article will be insufficient, and if the oil is contained in an amount exceeding the above range, a content of the polymer resin will be insufficient so that there is concerned that a lamination is not properly performed.

In addition, the aerogel may be used in an amount of 1 to 20 parts by weight, preferably 5 to 10 parts by weight, based on the weight of the oil.

Hereinafter, a method of preparing a 3D printing composition for producing a three-dimensional article having a slippery surface according to the present invention will be described in detail.

The method of preparing the 3D printing composition of the present invention comprises the steps of: preparing a polymer solution by dissolving a polymer resin in a first solvent; preparing an oil solution by dissolving an oil in a second solvent; and blending the polymer solution and the oil solution.

In a preferred embodiment of the invention, it is preferred that the oil solution contains an aerogel. The aerogel may be contained in an amount of 1 to 200 parts by weight based on the weight of the oil. In terms of the printing, the aerogel is most suitably 20 parts by weight, but may be added up to 200 parts by weight so as to strengthen a mechanical strength depending on the purpose.

According to the present invention, the polymer resin is dissolved in a solvent to form a liquid phase at a room temperature and the lubricating oil is dissolved in a separate solvent to form a liquid phase, and then the polymer resin and the lubricating oil in the liquid phase are blended such that the polymer resin is well blended with the lubricating oil. This blending of the polymer resin and the lubricating oil was intended to prevent the polymer resin from curing easily or the lubricating oil from evaporating easily at a high temperature.

The first solvent and the second solvent may be each independently selected from dichloromethane (DCM), tetrahydrofuran, dioxane, methylethylketone (MEK), dimethylformamide (DMF), and the like, and it is preferable to use a suitable solvent to meet the type of the polymer resin.

In a preferred embodiment of the present invention, it is preferable that the first solvent is the same solvent as the second solvent.

The polymer solution preferably has a concentration of 0.03 to 0.30 g/mL, and more preferably, the concentration of 0.05 to 0.15 g/mL.

The oil solution preferably has a concentration of 10 to 50% (v/v), and more preferably, the concentration of 15 to 30% (v/v).

In the present invention, the blending of the two solutions is preferably continuously stirred while adding the polymer solution to the oil solution little by little.

It is preferable that a total concentration of the 3D printing composition prepared by blending the two solutions is 0.05 to 0.30 g/mL.

The 3D printing composition prepared by the above method according to the present invention may be made of a filament for a 3D printer.

Specifically, if the 3D printing composition of the present invention is cured by evaporating a solvent at room temperature, it can exert a similar performance even after dissolving by adding heat. Therefore, in the course of curing the 3D printing composition of the present invention, it is possible to achieve a shape of the filament for a desired 3D printer through an additional cutting process after the printing composition is formed or cured in the shape of the filament using an extrusion or molding process.

It is preferable that the filament for the 3D printer has a standard that can be used in a commercially available 3D printer.

The filament for the 3D printer of the present invention preferably may have a diameter of 0.8 to 4.0 mm, and more preferably 1.5 to 3 mm. If the diameter of the filament is less than 0.8 mm, it may be too thin for the printer device to easily supply the filament or the filament may be pressed so that it cannot be discharged and thus a printing speed may be slowed down. In addition, if the diameter of the filament is more than 4.0 mm, a solidification rate is slow and it is difficult to melt the filament, whereby a precision of the printed sculpture may be deteriorated.

The 3D printing composition according to the present invention can implement an article of a three-dimensional shape having a slippery surface through a simple 3D printing technique. When an ink composition for the 3D printing containing the oil is output, the output is cured by a liquefaction lamination method while the solvent is evaporated, and as a result, the output has the inner surface and the outer surface, both of which are slippery, due to the property of the ink. By this method, it is possible to easily provide the slippery surface to the article of the three-dimensional shape, which was difficult to form the slippery surface using the conventional coating technique.

In a preferred embodiment of the present invention, the article having the slippery surface may further comprise a material through which the lubricating oil cannot be permeated.

For example, the coating composition of the present invention can be used to produce a zero-residue container.

The zero-residue container is a self-cleanable container, and the coating composition of the present invention and the material through which the oil is not permeated are printed at once to form the inner surface of the container having the slippery surface and the outer surface of the container having the material through which the lubricating oil is not permeated.

A material that can be applied to the outer surface of the zero-residue container may include glycol-modified polyethylene terephthalate (PETG), but is not limited thereto.

A coating composition that can be used on the inner surface of the zero-residue container may preferably include an edible oil, for example, a silicone oil.

In a preferred embodiment of the present invention, the coating composition of the present invention can be used to produce an antibacterial catheter.

In the medical field, the catheter is widely used as a carrier for a body fluid, a drug, a medical equipment, and the like. However, a bio membrane was easily formed on the surface of a tube so that there was a high possibility of clogging the tube or contaminating the tube by a bacteria.

In case of a medical catheter, the slippery surface and the antibacterial property are essential. The conventional catheter was used after impregnating a rubber catheter with an oil for a certain period of time so as to give the slippery surface. However, in case of the catheter impregnated with the oil, there are problems that an inner diameter thereof decreases due to the oil and that the slipperiness of the surface does not last for a long time because the oil comes out even with a little use.

If a catheter having a slippery surface is produced using the coating composition according to the present invention, the catheter having the slippery surface can be used immediately without performing a separate process for impregnating the oil, and the slippery surface of the catheter can last for a long time because the oil does not escape even when used for a long time. In addition, since the catheter can be produced to have a desired mechanical property and a desired standard, it can be suitably used to meet the application.

It is preferred that the coating composition for producing the catheter comprises a mineral oil, for example, a clove oil. If the coating composition comprises the clove oil, the produced article exhibits an antibacterial property, and thus is preferable for the medical use.

The polymer resin for producing the catheter may preferably include a silicone resin or a polyurethane resin from the viewpoint of a flexibility.

When the silicone resin is used as the polymer resin, a silicone oil is used as the lubricating oil because it is excellent in a compatibility. However, the clove oil may interfere with a crosslinking of the silicone resin when it is used in a large amount.

Therefore, the clove oil is preferably used in an amount of 5 to 30% by weight based on the total weight of the lubricating oil.

The article having the slippery surface that can be produced using the coating composition of the present invention are economical and energy efficient for the fields which requires a lower ice adhesion in an aircraft, a ship, an automobile, and the like, as well as the fields which requires an anti-biofouling, and a self-cleaning, and therefore can be used in various industries.

EXAMPLES

Hereinafter, the present invention will be described in more detail through the following Examples. However, these Examples are intended to show some experimental methods and compositions to illustrate the present invention by way of example, and the scope of the present invention is not limited to these Examples.

Preparation for Experiment

Production of Slippery Blend Ink

A silica gel with a particle size of 2 to 20 μm was purchased from REM-tech.

PDMS was purchased from Dow Corning.

A polylactic acid (PLA) was dissolved in a dichloromethane (DCM) at a ratio of 1:6 (w/w) and stirred for 24 hours.

A composition which is used for a UV curing process was blended with 5% by weight of Darocure 1173, a photo initiator of Fluorolink MD700.

The PDMS was blended with a curing agent in a weight ratio of 10:1. The coating compositions blended in composition ratios described in each experimental example were stirred at 2000 rpm for 3 minutes using a centrifugal mixer (Thinky, ARE-310).

Hereinafter, the coating composition for producing a three-dimensional article is referred to as a Slippery Blend or a Slippery Blend ink.

3D Printing of Slippery Blend Article

The Slippery Blend article which uses the Slippery Blend was produced by putting the Slippery Blend ink into a syringe barrel, removing an air, and then performing a 3D printing using a gauge tapered tip of 200 μm as a spray nozzle. Printing which uses a solvent casting was performed with a direct ink-writing system that applies a motor-action.

Experimental Example 1: Measurement of Rheological Property of Ink

Analysis of a rheological property of the Slippery Blend ink prepared based on PFPE, PDMS and PLA polymer resins was performed.

For measurement, a DHR-3 Rheometer (TA Instruments) having a gap of 1000 μm and a flat plate geometer of 40 mm was used. A vibration test for measuring a storage modulus and a loss modulus at different stress changes was performed while changing the stress from 0.1 Pa to 1000 Pa at a fixed frequency of 1 Hz. A yield stress was defined as the value when the storage modulus fell down to 90% of an initial value.

The storage modulus (G') and the loss modulus (G") against shear stresses of the PFPE and the PFPE-based Slippery Blends are shown in Table 2 below. In Table 2, the unit is Pa, and the PFPE Slippery Blend was prepared by blinding in a weight ratio of the PFPE:the fluorinated oil:the silica gel=(65:25:10).

TABLE 2

|  |  | Shear stress | |
| --- | --- | --- | --- |
| Type | | 1 | 50 |
| Slippery Blend (PFPE) | Storage modulus | 793 | 6 |
|  | Loss modulus | 189 | 31 |
|  | Crossover point between G' & G" | ≈10 | |
| PFPE | Storage modulus | 0.07 | 0.08 |
|  | Loss modulus | 1.99 | 1.98 |
|  | Crossover point between G' & G" | — | |

In Table 2 above, the storage modulus and the loss modulus of the PFPE were not changed and indicated a parallel profile despite of an increase in the vibration stress. However, the Slippery Blend to which the silica aerogel particles was added indicated that the storage modulus was more predominant (G'>G") at a low shear yield stress ($\tau_y$<10 Pa), but as the shear stress increased ($\tau_y$>10 Pa), the storage modulus was rapidly decreased, so the loss modulus was more predominant.

The storage modulus (G') and the loss modulus (G") against the vibration stress of the PDMS and the PDMS-based Slippery Blend are shown in Table 3 below. In Table 3, the unit is Pa, and the PDMS Slippery Blend was prepared by blending in a mixing ratio of the PDMS:the mineral oil:the silica gel=(70:25:5).

TABLE 3

|  |  | Shear stress | |
| --- | --- | --- | --- |
| Type | | 1 | 50 |
| Slippery Blend (PDMS) | Storage modulus | 35,664 | 857 |
|  | Loss modulus | 11,422 | 1,820 |
|  | Crossover point between G' & G" | ≈160 | |
| PDMS | Storage modulus | 141,909 | 471 |
|  | Loss modulus | 40,231 | 1,127 |
|  | Crossover point between G' & G" | ≈1,000 | |

In Table 3 above, it was indicated that the shear yield stress of the PDSM-Slippery Blend containing the aerogel is higher than that of the blend of the PDMS and the oil without the aerogel.

This means that the ink can maintain a shape of the filament even at a higher shear stress, and can be printed by a narrower nozzle.

The storage modulus and the loss modulus according to an evaporation time of the PLA solvent and the PLA Slippery Blend solvent which were dissolved in the DCM are shown in Table 4 below. In Table 4, the unit is Pa, and the PLA Slippery Blend was prepared by blending in a mixing ratio of the PLA:the mineral oil:the silica gel=(70:20:10).

TABLE 4

|  |  | Time (sec) | |
| --- | --- | --- | --- |
| Type | | 30 | 300 |
| Slippery Blend (PLA) | Storage modulus | 1.63 | 3,324 |
|  | Loss modulus | 2.98 | 1,400 |
|  | Crossover point between G' & G" | 100 sec | |
| PLA | Storage modulus | 14.4 | 32,017 |
|  | Loss modulus | 29.1 | 5,090 |
|  | Crossover point between G' & G" | 100 sec | |

In Table 4 above, the storage modulus and the loss modulus could be confirmed immediately after the solvent was removed. A solidification of the PLA Slippery Blend could be performed immediately after it was discharged from the nozzle.

The above result is significant in that it means that a blend of the polymer resin and the lubricating oil having the properties that cannot maintain a shape of the three-dimensional article can also maintain the three-dimensional shape by adding the aerogel.

Experimental Example 2: Production of 3D Article

In order to confirm a possibility of the 3D printing of the Slippery Blend, a scaffold was prepared using the PDMS-Slippery Blend by a micro nozzle (diameter of 200 μm).

Figure 2:
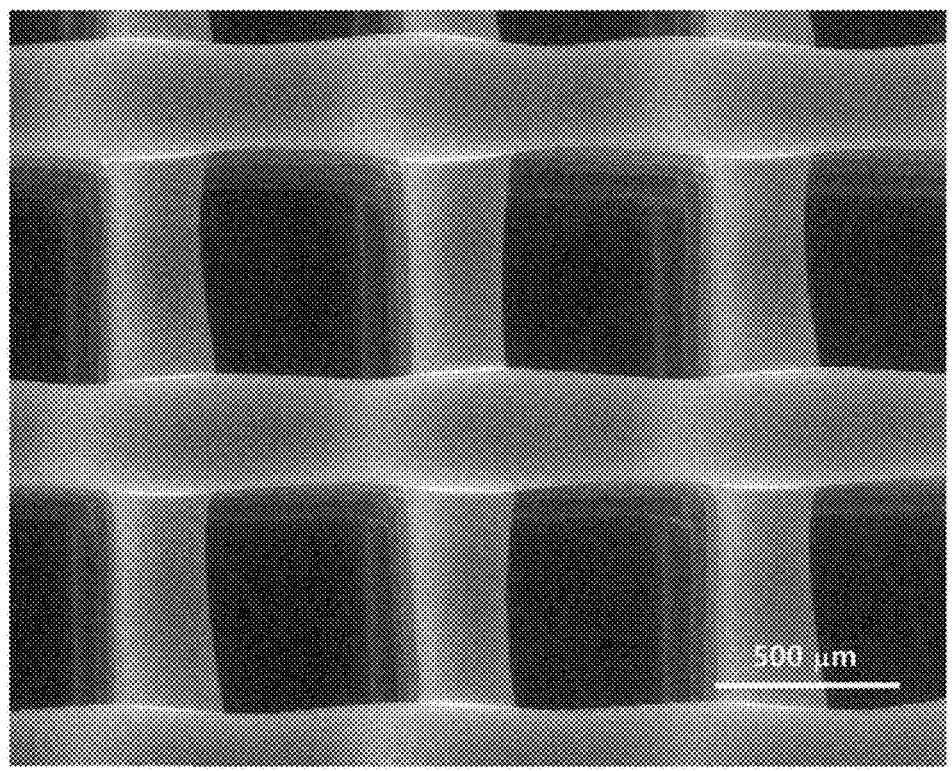
FIG. 2 shows an image of a scaffold prepared using a PDMS-Slippery Blend.

As can be seen in FIG. 2, due to a shear mint property and a non-Newtonian fluid property, the Slippery Blend ink was easily extruded from a nozzle of a micro-size to maintain a shape of the filament. The produced scaffold was composed of a filament having a diameter of about 250 μm and a space of about 800 μm.

This means that a three-dimensional article of a micro-unit can be produced using the coating composition of the present invention.

Experimental Example 3: Measurement of Mechanical Property

In order to test a mechanical property of the Slippery Blend, a tensile strength and a shore hardness thereof were measured.

A dumbbell-shaped sample for testing the tensile strength was prepared according to a standard DIN 53504. The test was performed at a speed of 500 mm/min using a loading cell of 1 kN. A sample for measuring the hardness was prepared with a thickness of 2 cm. The shore A hardness was measured using a Shore A durometer.

The mechanical properties of the Slippery Blend materials according to different contents of the polymer resin, the lubricating oil and the aerosol are shown in Table 5 below.

TABLE 5

| PDMS Elastomer [wt %] | Mineral Oil [wt %] | Silica Aerogel Particle [wt %] | Ultimate Tensile Strength [Mpa] | Elongation at Break [mm/min] | Hardness [Shore A] |
|---|---|---|---|---|---|
| 100.00 | 0.00 | 0.00 | 5.97 ± 0.32 | 3.22 ± 0.18 | 47.70 ± 1.15 |
| 70.00 | 25.00 | 5.00 | 3.07 ± 0.17 | 2.48 ± 0.17 | 25.20 ± 0.91 |
| 80.00 | 7.46 | 11.94 | 8.11 ± 0.52 | 4.24 ± 0.19 | 65.00 ± 2.10 |

In Table 5 above, an ultimate tensile strength of the PDMS-Slippery Blend containing 30% by weight of the oil and aerogel blend was reduced by 48.6% compared to the PDMS without the oil.

As a content of the silica aerogel increased, the ultimate tensile strength increased, and the Slippery Blend containing 11.9% by weight of the silica aerogel indicated the ultimate tensile strength of about 8.1 MPa, which shows a higher strength than that of the PDMS alone indicating about 6.0 MPa.

In Table 5 above, although the hardness was significantly reduced with the addition of the lubricating oil, it can be confirmed that adding the silica aerogel indicated a higher hardness despite the addition of the lubricating oil.

From these results, it can be seen that the addition of the aerogel can greatly improve the mechanical properties of the blend of the polymer resin and the lubricating oil.

Experimental Example 4: Analysis of Lubrication Performance of Slippery Blend

In order to analyze the lubrication performance of the Slippery Blend article, measurement of a critical sliding angle was performed on various polar and non-polar liquid droplets.

Wetting properties for the liquid droplets with various surface tensions as shown in Table 6 below were measured using a contact angle measurement stage. The droplets of 10 μl were dropped at 10 different positions on the PDSM and PFPE-based samples having the compositions of Experimental Example 1. The sliding angle was measured by dropping 10 μl of the droplets on the tilted stage using a high-speed camera.

TABLE 6

| | Target liquid (surface tension, mN/m) | | | | |
|---|---|---|---|---|---|
| Sample type | Petroleum ether (17.5) | Chloroform (26.7) | Olive oil (32.0) | Ethylene glycol (47.3) | Water (72.1) |
| PDMS | — | — | 34.1 ± 2.8 | 33.3 ± 3.1 | 69.3 ± 4.2 |
| PDMS-Slippery Blend | — | — | 9.2 ± 2.1 | 9.0 ± 3.1 | 7.5 ± 1.4 |
| PFPE | 27.2 ± 2.6 | 25.3 ± 1.9 | 25.9 ± 2.1 | 26.2 ± 2.5 | 40.1 ± 3.9 |
| PFPE-Slippery Blend | 4.7 ± 1.6 | 5.3 ± 1.1 | 4.1 ± 1.7 | 3.5 ± 1.3 | 3.3 ± 1.1 |

In Table 6 above, the PDMS-Slippery Blend indicated a low critical sliding angle of 10° or less for the water, the ethylene glycol, and the olive oil. However, the PDMS-Slippery Blend did not show the lubrication property for volatile solvents such as chloroform and petroleum ether, which is because the PDMS swells easily against the volatile solvents, and the mineral oil is easily dissolved in such a solution so that it cannot maintain a lubricating layer.

On the other hand, the PFPE-based Slippery Blend which uses the fluorinated lubricating oil exhibited a very low sliding angle of about 5° or less for all target liquid droplets.

This means that the coating composition of the present invention can be used to prepare an omniphobic (superhydrophobic) article.

Experimental Example 5: Production of Self-Cleanable Container

It was intended to produce a functional article by printing different types of materials at once using a Slippery Blend platform.

Figure 3A:
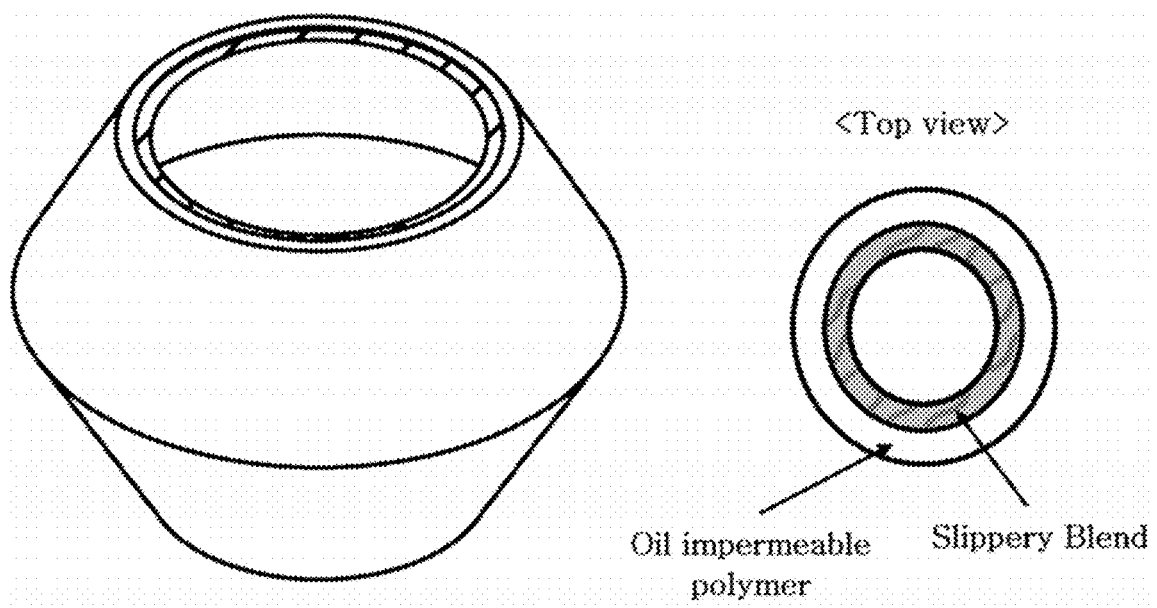
FIG. 3a shows a conceptual diagram of a self-cleanable container made of two foreign materials of a Slippery Blend and a PETG using a two-nozzle DIW printing mode.

As shown in FIG. 3a, a self-cleanable container was produced using a two nozzle DIW printing method.

In order to prevent the lubricating oil from spreading through the outer surface of the container while maintaining the lubricity at the inner surface of the container, the PDMS-Slippery Blend ink was used to produce the inner surface of the container, and the PETG filament was used to produce the outer surface of the container.

Figure 3B:
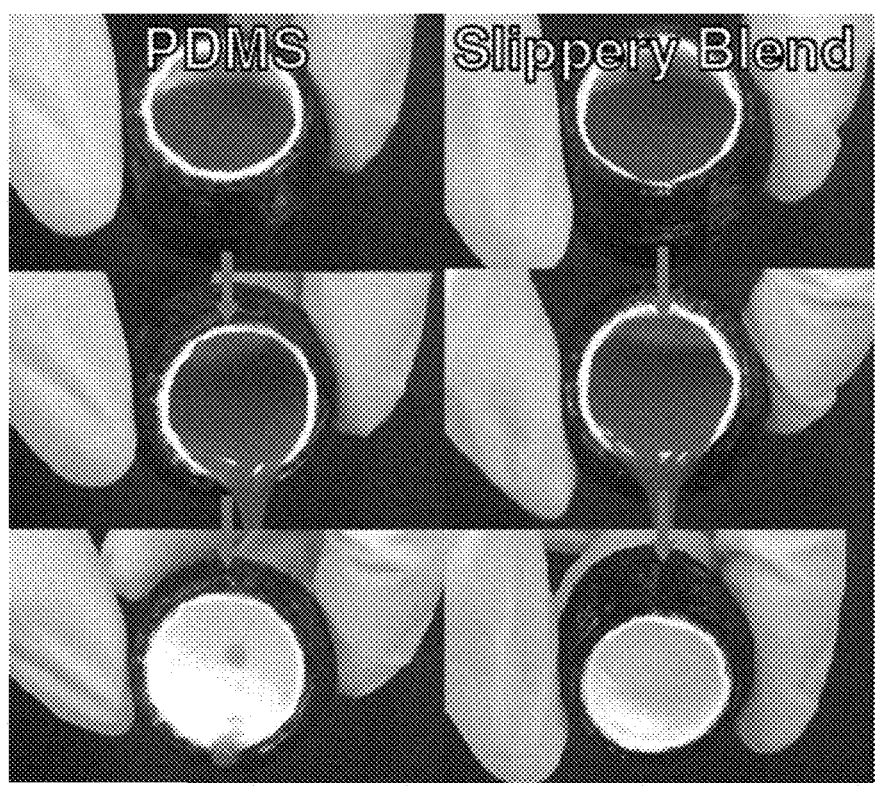
FIG. 3b shows a comparison of self-cleaning performances when pouring a ketchup into the container of FIG. 3 and pouring it out.

As shown in FIG. 3b, the produced container could easily remove sticky contents without special measures.

Experimental Example 6: Measurement of Optical Transmittance

In order to measure the optical transmittance of the PDMS-based lubricating article, a UV-Visible Spectrophotometer (Lambda 650S, Perkin Elmer) was used.

The measurements were performed at wavelengths of 400, 600 and 800 nm, respectively. The PDMS-based samples were drop-cast onto a slide glass at 500 μm, and the samples were separated from the slide glass to minimize an effect of the slide. The results are shown in Table 7 below.

In Table 7, a blend of the PDMS and the silica gel was blended at a weight ratio of 93:7, and the Slippery Blend was prepared with the composition described Experimental Example 1.

TABLE 7

| Wavelength | Transmittance (% T) | | |
|---|---|---|---|
| | PDMS | PDMS + Aerogel | Slippery Blend |
| 400 nm | 85.7 | 83.5 | 86.8 |
| 600 nm | 90.0 | 85.3 | 89.5 |
| 800 nm | 92.4 | 86.2 | 91.1 |

In Table 7 above, the transmittances of the PDMS and the PDMS-Slippery Blend at 400 to 800 nm were 85.7 to 92.4% for the PDMS, and 86.8 to 91.1% for the PDMS Slippery Blend. This means that both the PDMS and PDMS-Slippery Blend substrate indicates transparency.

Meanwhile, the PDMS-aerogel substrate had a slightly reduced permeability to 83.5 to 86.2%, which is because the aerogel scattered a light. On the other hand, the PDMS-Slippery Blend showed more excellent transparency than the PDMS substrate, which is because the lubricating oil had a refractive index similar to that of the PDMS to further reduce reflection of the light.

Therefore, the coating composition of the present invention can produce an optically transparent article having a slippery property.

Experimental Example 7: Ice Adhesion Test

An experiment was performed to check an ice adhesion according to a content of the lubricating oil.

Samples having various contents of the lubricating oil were prepared by drop-casting on a flat glass to a thickness of 500 μm. A load cell was used with a sensitivity of 5 mN.

After the sample was fixed to a stage, a plastic cylinder of 0.75 cm in a diameter and 1 cm in a height was placed vertically, and 200 μl of a demineralized water was sprayed. After the ambient temperature was maintained at −15° C. for 1 hour, the end of a force probe was placed apart at a distance of 1 mm from the sample surface, and then a force required to remove the ice was measured by pushing the sample at a rate of 0.05 mm/s. The results are shown Table 8 below.

TABLE 8

| Mixing Ratio [%] | | | Ice adhesion strength [kPa] |
|---|---|---|---|
| 100% PDMS | — | — | 159.7 |
| 100% PFPE | — | — | 299.5 |
| 85% PDMS | 12.5% Silicone Oil | 2.5% Silica Aerogel | 88.5 |
| 85% PFPE | 12.5% Fluorinated Oil | 2.5% Silica Aerogel | 73.3 |
| 70% PDMS | 25% Silicone Oil | 5% Silica Aerogel | 60.3 |
| 70% PFPE | 25% Fluorinated Oil | 5% Silica Aerogel | 11.2 |

From Table 8 above, it can be confirmed that the PDMS-Slippery Blend containing 15% of a blend of the silicone oil and the aerogel has an ice adhesion reduced by 44.6%, compared to a blend which does not contain the oil. In addition, the sample containing 30% of a blend of the silicone oil and the aerogel showed the ice adhesion of 60.3 kPa, which was reduced by 62.3% compared to the PDMS alone.

This tendency was also indicated in the same in the PFPE-based Slippery Blend. The PFPD-Slippery Blend containing 30% of the fluorinated oil showed the ice adhesion significantly reduced by 96.2%, compared to a sample without the oil.

Experimental Example 8: Antibacterial Test

A bacterial adhesion test was carried out according to JIS Z2801.

*E. coli* EG1655 was used as a strain. A sample was drop-cast to a thickness of 1 mm, cut into the size of 5×5 cm$^2$, placed in an autoclave and sterilized at 100° C. The sterilized sample was placed in a petri dish and 400 μl of the *E. coli* medium (~10$^8$ CFU/mL) was placed on the sample. The medium was covered with a sterile polyester film (4×4 cm$^2$) to control the contact area therebetween. The sample was incubated at 36° C. for 24 hours. After incubation, the sample was carefully washed with a PBS solution to remove bacteria that were not adhered.

After removing the bacterial film from the sample surface using a cotton swab, the sample and the cotton swab were placed in a conical tube containing 20 mL of the PBS solution. The conical tube was sonicated for 10 minutes and diluted 1000 times. Thereafter, 200 μl of the solution was incubated in an LB agar plate for 24 hours.

With respect to the PLA and the PDMS-based Slippery Blend, the number of strains in case the oil was not added, in case only the olive oil was added, and in case the olive oil and the clove oil was added in a weight ratio of 5:1, is shown in Table 9 below.

TABLE 9

| Mixing Ratio [%] | | | Number of Colonies [CFU/cm$^2$] |
|---|---|---|---|
| 100% PLA | — | — | 698.750 |
| 100% PDMS | — | — | 361.250 |
| 85% PLA | 12.5% Olive Oil | 2.5% Silica Aerogel | 78.750 |
| 85% PDMS | 12.5% Olive Oil | 2.5% Silica Aerogel | 46.250 |
| 70% PLA | 20.8% Olive Oil + 4.2% Clove Oil | 5% Silica Aerogel | 9 |
| 70% PDMS | 20.8% Olive Oil + 4.2% Clove Oil | 5% Silica Aerogel | 8 |

Even in case only the olive oil was added in the PLA and the PDMS-based Slippery Blend, it was confirmed that some antibacterial activity occurred (83.2% and 85.7%, respectively).

In case the clove oil was added, it was confirmed that the number of strains decreased to 99.9% (PLA) and 98.2% (PDMS), which indicates an excellent antibacterial activity.

This phenomenon is thought to be caused because an eugenol, the main component of the clove oil, damages the cell membrane of the bacteria to negatively affect a metabolism and a diffusion of the bacteria.

Experimental Example 9: Production of Antibacterial Catheter

An antibacterial Slippery Blend catheter tube was produced to confirm that the antibacterial Slippery Blend is actually applicable.

Figure 4:
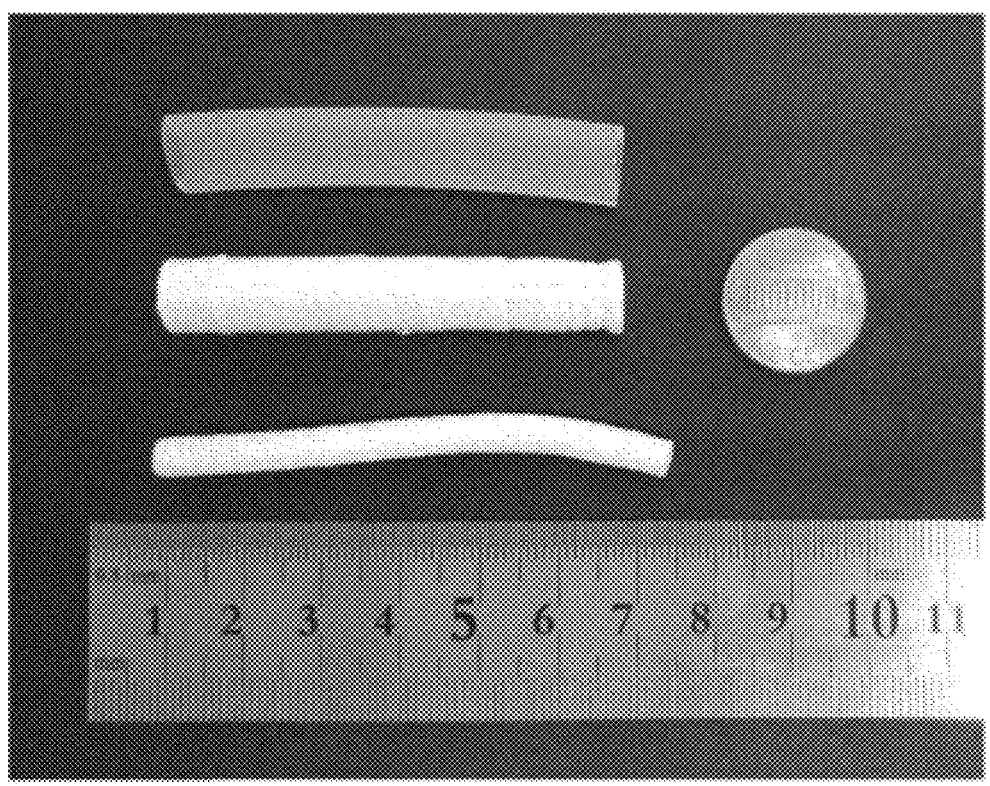
FIG. 4 is an image of a silicone tube produced by a printing mode using a commercially available medical silicone tube and a PDMS-Slippery Blend.

FIG. 4 is images of a tube having a length of 6 cm, an inner diameter of 7 mm and a thickness of 0.8 mm, which was produced by the printing manner using the PDMS-Slippery Blend, and a commercially available medical silicone tube. The tubes were produced using a non-reactive mineral oil and a silicone elastomer which were approved by the FDA for biocompatibility.

In order to confirm an activity of preventing a biological adherence on the produced tubes, a fluidizing bacterial adhesion test was performed.

A *P. aeruginosa* which was cultured overnight was mixed in a LB Broth at a ratio of 1:100 and continuously rotated using a Peristaltic pump.

A sterilized silicone tube (1.0:6.4 mm, Cole Parmer, Masterflex L/S 17) was connected to the pump such that an inlet of the pump was immersed in a medium and an outlet thereof was connected to the tube of the Slippery Blend and was placed in the medium.

Formation of a bio membrane was checked at 8 hours, 16 hours, and 24 hours, and the comparison results thereof were shown in Table 10 below.

TABLE 10

| Culture time | Optical Density [A595] | |
|---|---|---|
| [hours] | Commercial Silicone Tube | Slippery Blend Tube |
| 0 h | 0 | 0 |
| 8 h | 0.09 | 0.02 |
| 16 h | 1.97 | 0.24 |
| 24 h | 2.34 | 0.67 |

In Table 10 above, the Slippery Blend tube showed the optical densities reduced to 87.6% at 16 hours and to 71.4% after 24 hours, when the bio membranes began to form, compared to the commercially available medical silicone tube, which confirms that the antibacterial activity occurred.

Preparation Example 1: Preparation of 3D Printing Composition

Figure 5A:
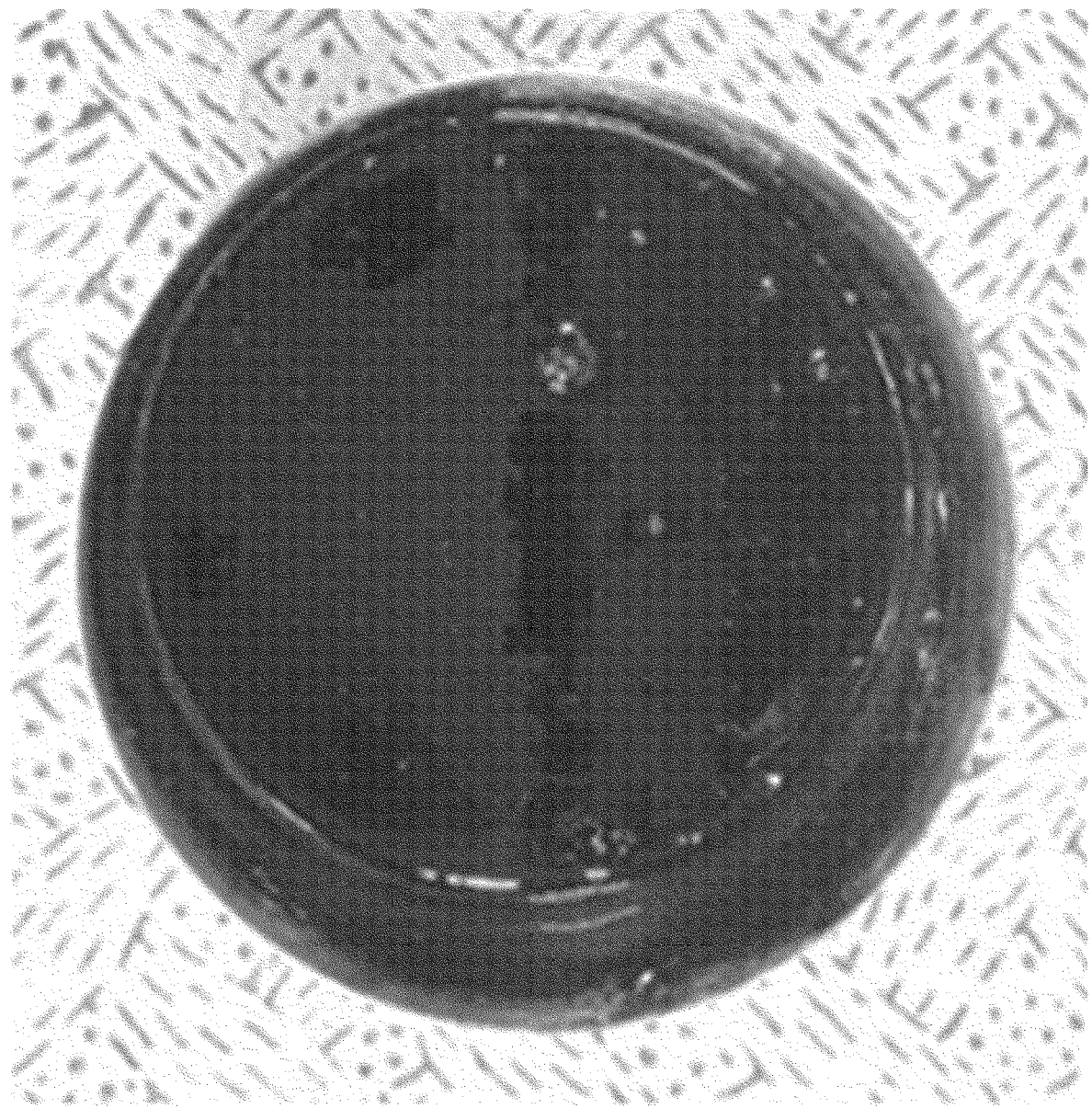
FIG. 5a shows a polylactic acid solution according to an embodiment of the present invention.

A polylactic acid solution was prepared by adding 5 g of polylactic acid to 80 mL of dichloromethane at a room temperature and stirring them until completely dissolved in a solvent (FIG. 5a).

Figure 5B:
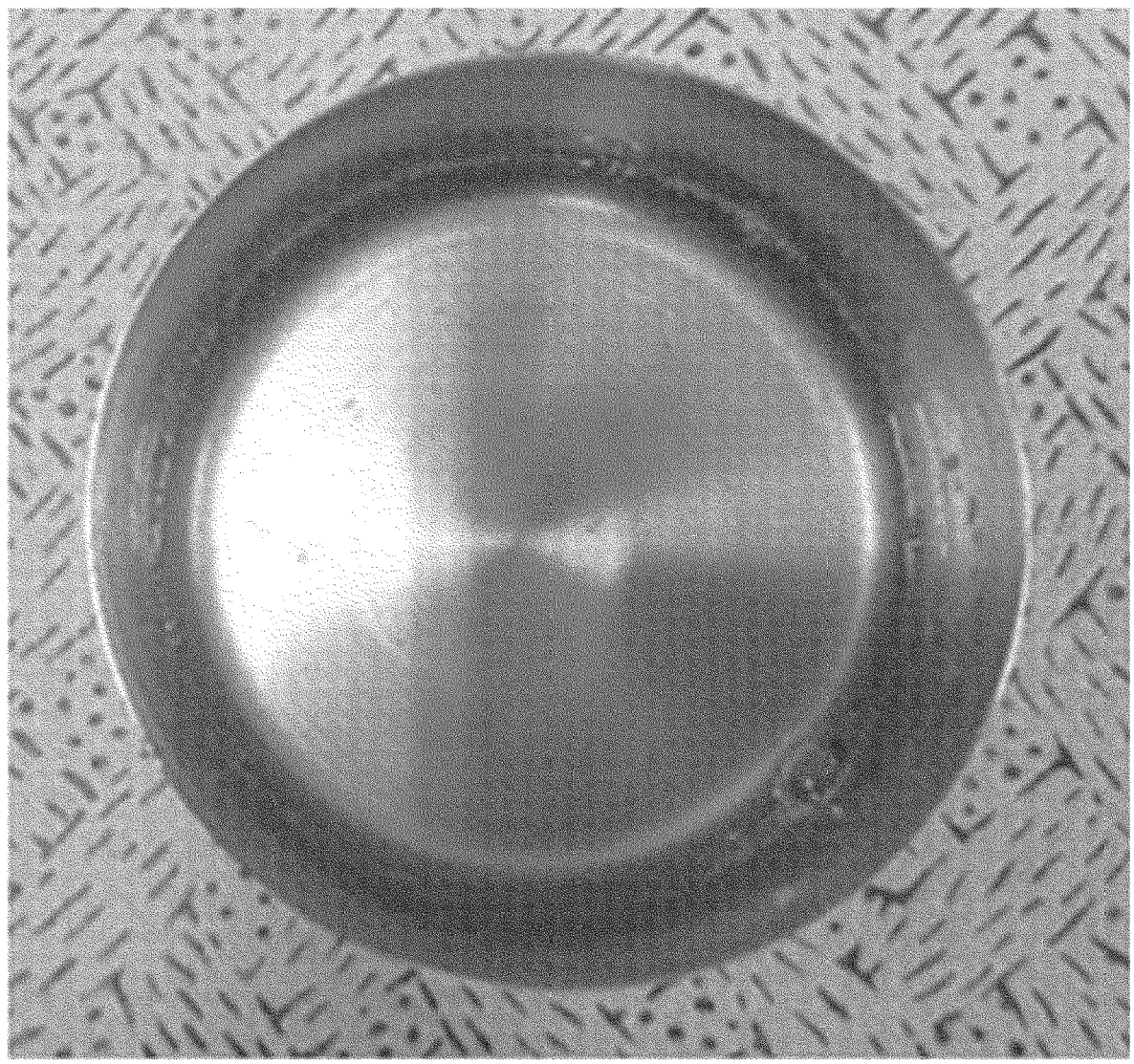
FIG. 5b shows an olive oil solution according to an embodiment of the present invention.

An olive oil solution was prepared by adding 5 mL of an olive oil and 1 g of a silica aerogel to 20 mL of dichloromethane and stirring them (FIG. 5b).

Figure 5C:
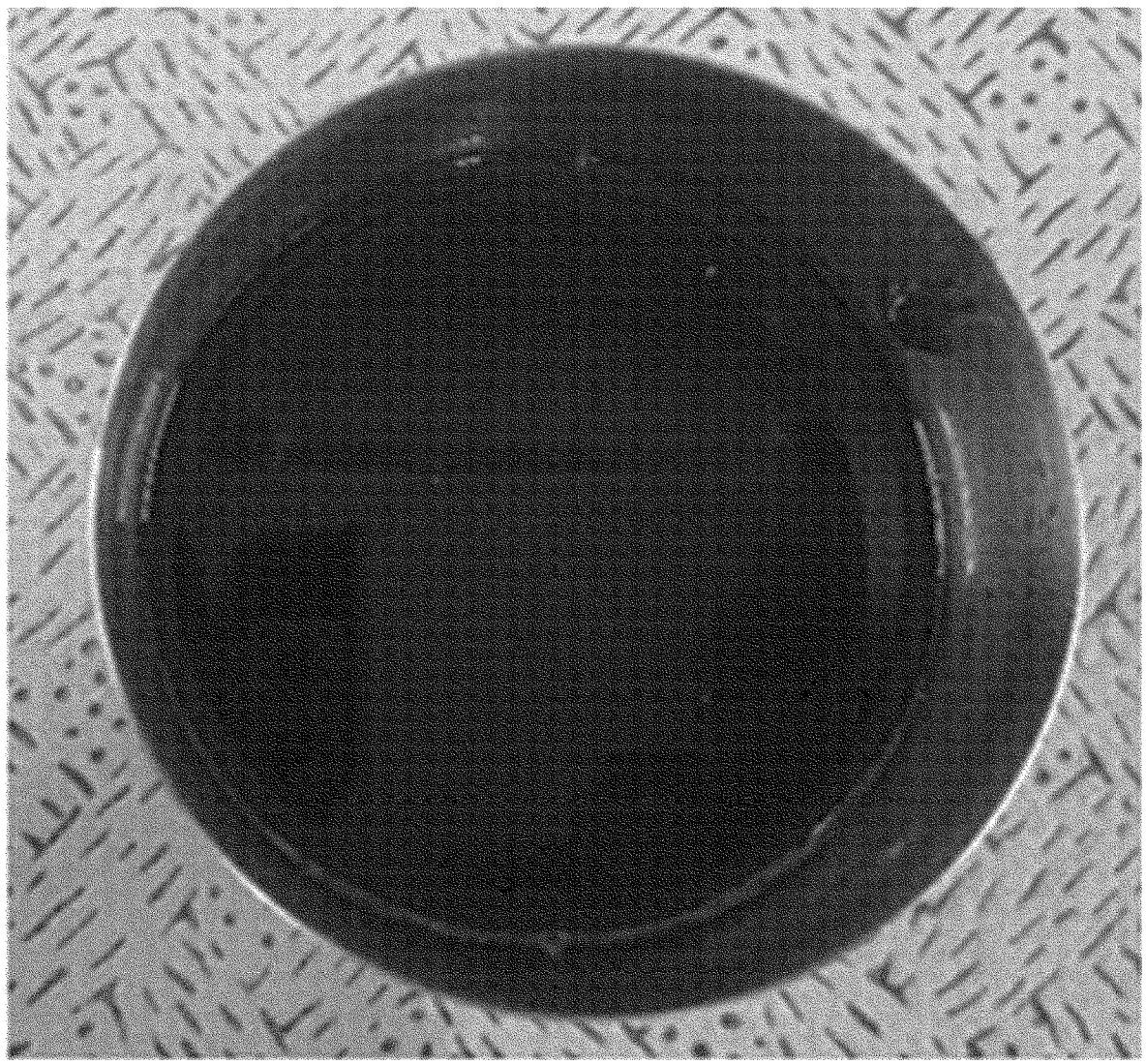
FIG. 5c shows a 3D printing composition according to an embodiment of the present invention.

A 3D printing composition was prepared by slowly adding dropwise the polylactic acid solution to the olive oil solution while stirring them (FIG. 5c).

Preparation Example 2: Production of Filament for 3D Printer

The 3D printing composition prepared by the Preparation Example 1 was supplied to an extruder through a hopper. The composition was melted and kneaded in the extruder and spun through a spinning nozzle. At this time, a temperature of a screw in the extruder was set to 200° C. The spun filament was cooled in an air to produce a filament for 3D printer having an average diameter of 1.75 mm.

Preparation Example 3: Production of Three-Dimensional Shape Having Slippery Surface The filament produced by the Preparation Example 2 was put into an FDM mode 3D printer having a nozzle diameter of 400 μm, and outputted in a manner of being laminated through a nozzle at a rate of 60 mm/s at a use temperature of 200° C.

Figure 6A:
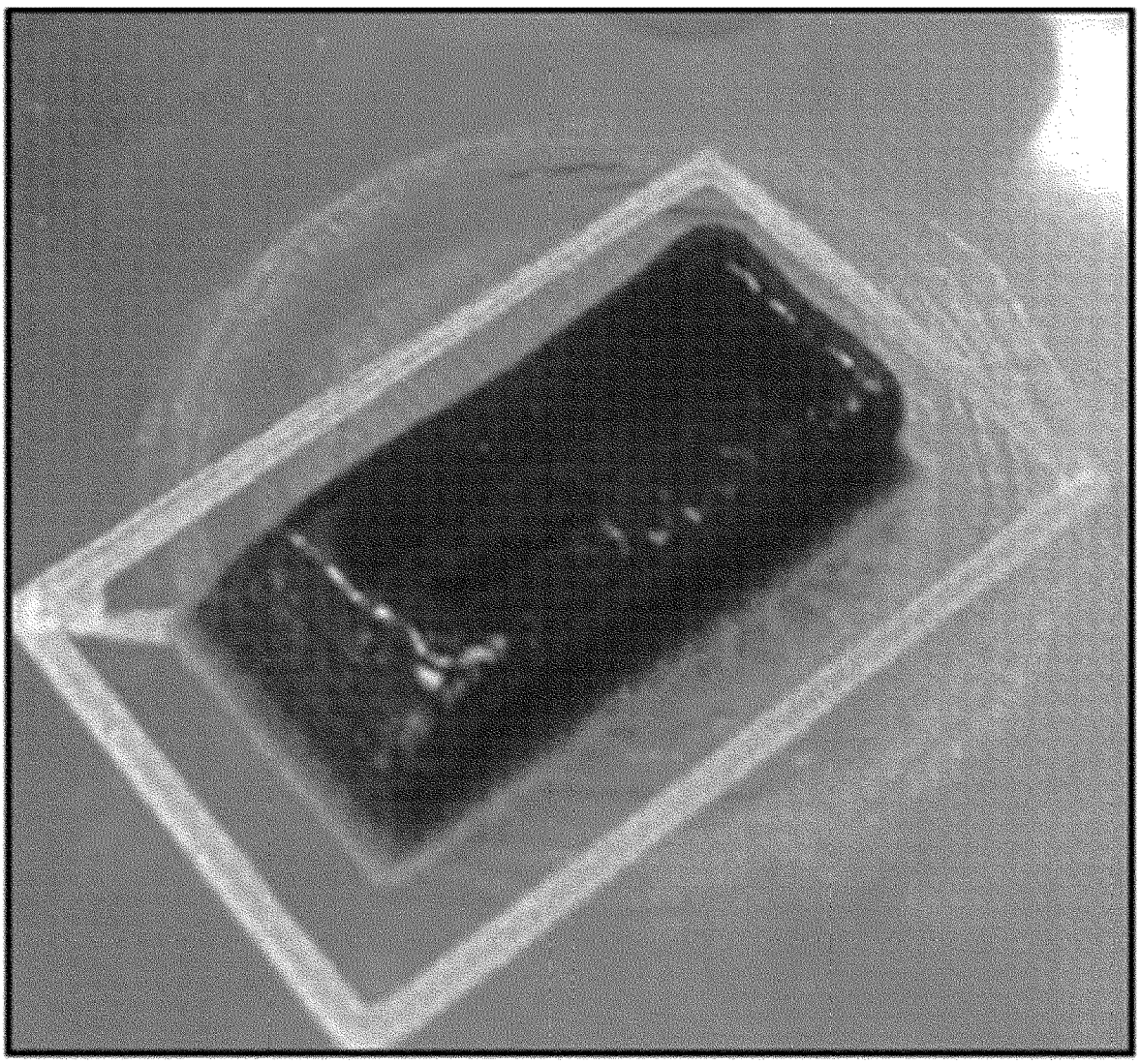
FIG. 6a shows a cuboid-shaped 3D article having a slippery surface according to an embodiment of the present invention.
Figure 6B:
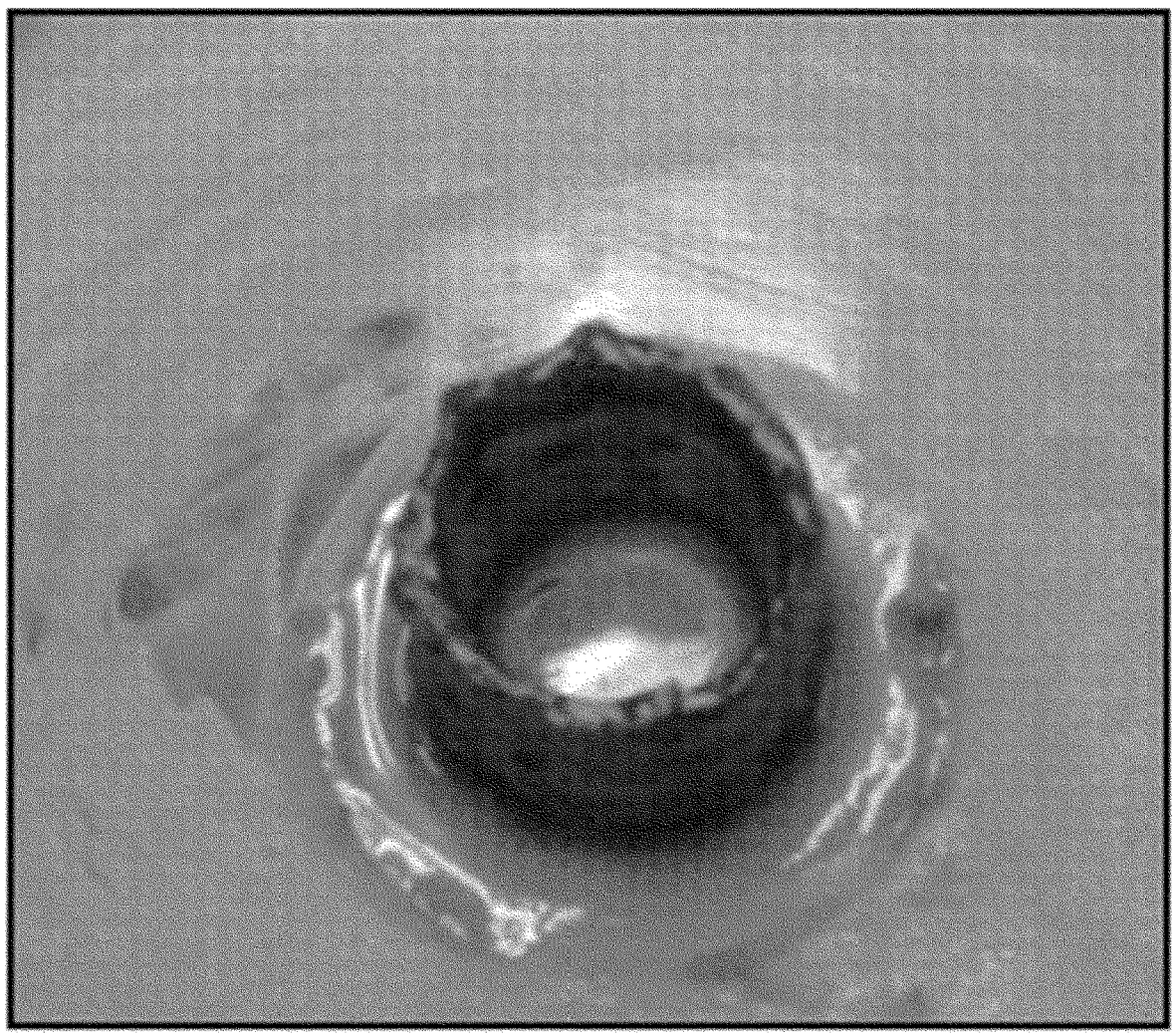
FIG. 6b shows a cylinder-shaped 3D article having a slippery surface according to an embodiment of the present invention.

As shown in FIG. 6, it was confirmed that a three-dimensional article in the shape of a rectangular parallelepiped (a) and a cylinder (b) was produced, and that the 3D printer composition of the present invention containing the oil could be applied to a commercialized 3D printer.

Experimental Example 10: Check of Slippery Property

This Example is to confirm a slippery property of the 3D printing composition prepared by the Preparation Example 1.

A slide glass was coated with the 3D printing composition prepared by the Preparation Example 1 and only a polylactic acid as a comparative example in a dip coating manner, and naturally cured by allowing a solvent to evaporate at a room temperature.

FIG. 7 is a view showing a movement of droplets for 6 seconds while coating the polylactic acid (a) and the composition (b) prepared by the Preparation Example 1 on the slide glass and tilting the slide glass to 10°.

Figure 7A:
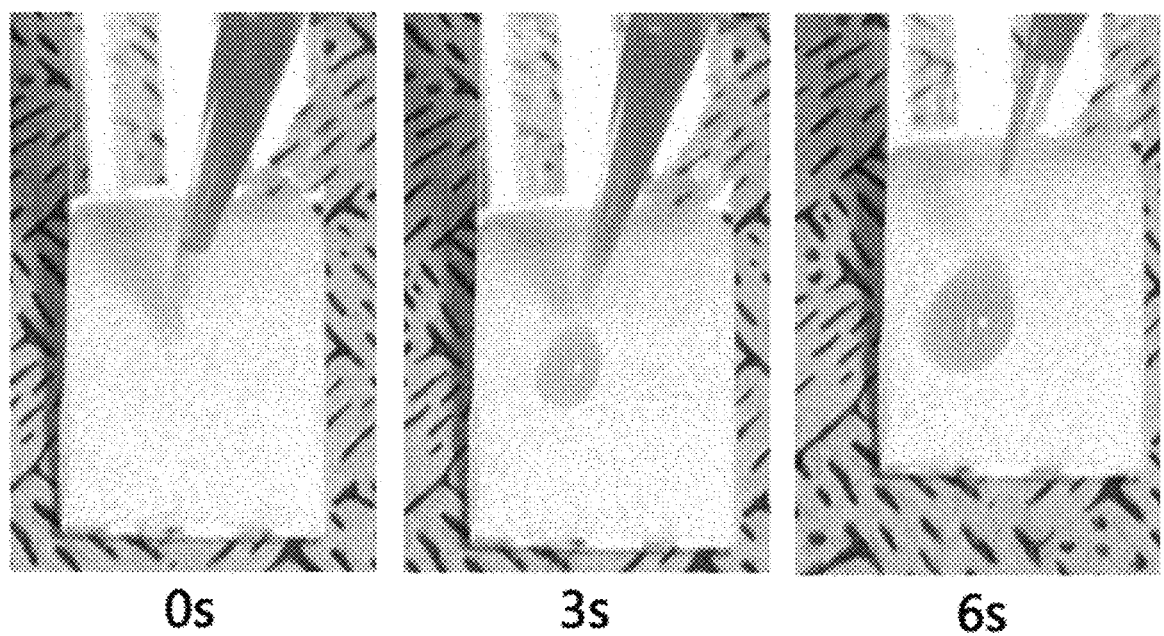
FIG. 7a shows a movement of a droplet on a coating of a polylactic acid according to Comparative Example of the present invention.
Figure 7B:
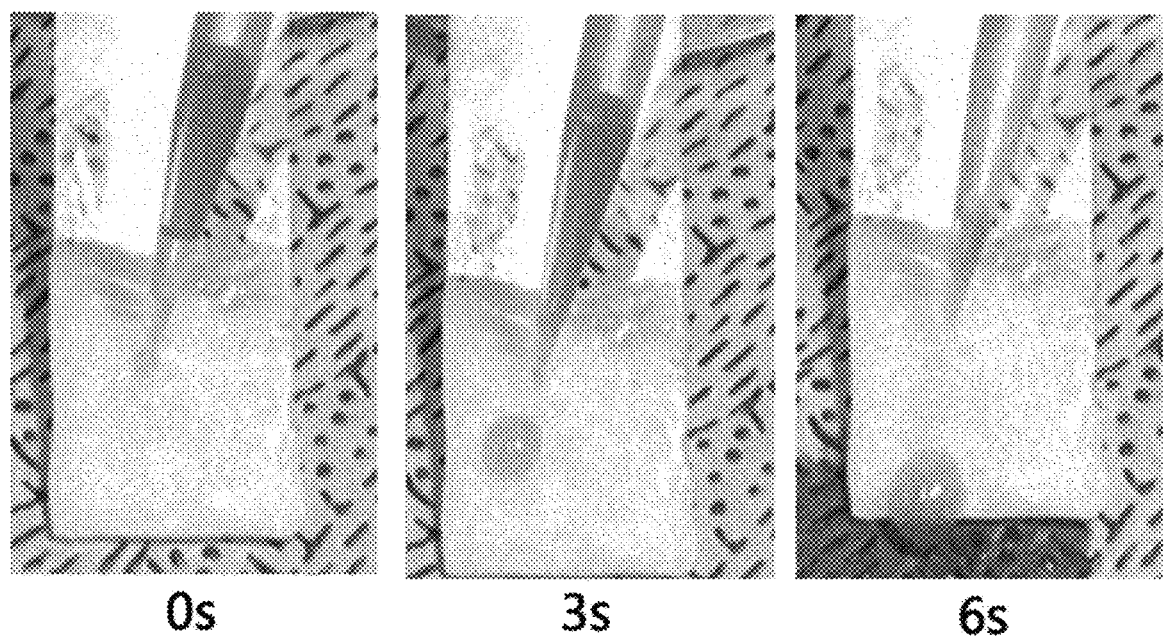
FIG. 7b shows a movement of a droplet on a coating of a 3D printing composition according to an embodiment of the present invention.

It can be confirmed in case of FIG. 7a, there was almost no movement of the droplets for 6 seconds, but in case of FIG. 7b, the droplets slipped down after 6 seconds.

The composition of the Preparation Example 1 was melted at 200° C., and then cooled again at a room temperature, to confirm whether the composition of the present invention could maintain the slippery property even when it was output with a 3D printer.

Figure 7C:
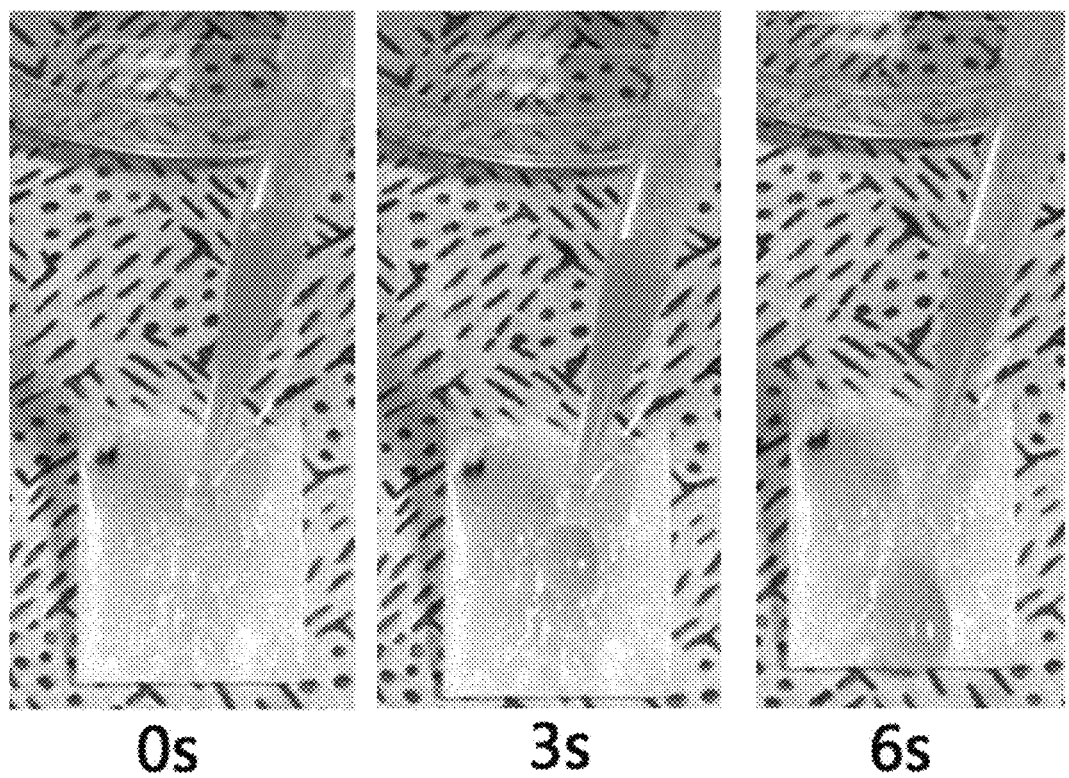
FIG. 7c shows a movement of a droplet after a 3D printing composition according to an embodiment of the present invention is melted at a high temperature and then solidified again.

As can be confirmed in FIG. 7c, the composition of the present invention that is hardened again after being melted by a high temperature still has a slippery surface to slip down the droplets.

As described above, since specific embodiments of the present invention have been explained in detail, those skilled in the relevant art will obviously appreciate that these concrete technologies are merely preferred embodiments and the scope of the present invention is not limited by these technologies. Accordingly, the substantial scope of the present invention will be defined by the appended claims and their equivalents.

What is claimed is:

1. A coating composition for producing an article, comprising a blend of a polymer resin, a lubricating oil, and an aerogel, wherein the coating composition is in a liquid-phase.

2. The coating composition according to claim 1, wherein the polymer resin is one or more selected from the group consisting of polydimethylsiloxane (PDMS), silicone, perfluoropolyether (PFPE), polyurethane (PU), thermoplastic polyurethane (TPU), polyimide (PI), polylactic acid (PLA), acrylonitrile butadiene styrene (ABS), high density polyethylene (HDPE), polycarbonate (PC), polystyrene (PS), polyester, polyolefin, polyamide, polyvinyl alcohol, N-vinyl pyrrolidone, N-vinyl caprolactam, dimethylacrylamide, hydroxyethylacrylamide, 2-acryloyloxyethyl isocyanate, isobornyl acrylate, tetrahydrofurfuryl acrylate, phenoxypolyethylene glycol acrylate, lauryl acrylate, benzyl acrylate, ethoxyethyl acrylate, phenoxyethyl acrylate, cyclic trimethylolformal acrylate, 6-hexanediol diacrylate, trimethylolpropane triacrylate, pentaerythritol tetraacrylate, tripropylene glycol diacrylate, tetraethylene glycol diacrylate, 1,1-(bisacryloyloxymethyl)ethyl isocyanate, polyester acrylate, and urethane acrylate.

3. The coating composition according to claim 1, wherein the lubricating oil is one or more selected from the group consisting of an olive oil, a fluorinated oil, a silicone oil, an essential oil, a paraffin oil, and a mineral oil.

4. The coating composition according to claim 1, wherein a content of the lubricating oil is 30 to 100 parts by weight based on 100 parts by weight of the polymer resin.

5. The coating composition according to claim 1, wherein a free energy for blending the polymer resin and the lubricating oil is greater than 0, and a free energy for blending the polymer resin, the lubricating oil and the aerogel is less than 0.

6. The coating composition according to claim 1, wherein the aerogel is one or more selected from a silica gel, a carbon aerogel and a graphene aerogel.

7. The coating composition according to claim 1, wherein a content of the aerogel is 1 to 200 parts by weight based on 100 parts by weight of the lubricating oil.

8. The coating composition according to claim 3, wherein a content of the essential oil is 10 to 100% by weight based on the total weight of the lubricating oil.

9. The coating composition according to claim 1, further comprising one or more solvents selected from the group consisting of dichloromethane (DCM), tetrahydrofuran, dioxane, methylethylketone (MEK) and dimethylformamide (DMF).

10. The coating composition according to claim 9, comprising the one or more solvents such that a concentration of the blend in the coating composition is 0.05 to 0.30 g/mL.

\* \* \* \* \*